United States Patent [19]

Wohlfahrt et al.

[11] Patent Number: 4,783,572

[45] Date of Patent: Nov. 8, 1988

[54] PROCESS FOR THE PREPARATION OF ETHYLENE-ETHANE MIXTURES

[75] Inventors: Klaus Wohlfahrt, Obernburg; Manfred Bergfeld, Erlenbach-Mechenhand; Hans-Georg Zengel, Kleinwallstadt, all of Fed. Rep. of Germany

[73] Assignee: Akzo N.V., Arnhem, Netherlands

[21] Appl. No.: 836,984

[22] Filed: Mar. 6, 1986

[30] Foreign Application Priority Data

Mar. 11, 1985 [DE] Fed. Rep. of Germany ....... 3508571

[51] Int. Cl.$^4$ .............................................. C07C 2/00
[52] U.S. Cl. .................... 585/500; 585/415; 585/417; 585/418; 585/654; 585/656; 585/658; 585/661; 585/700; 585/943
[58] Field of Search ............... 585/500, 415, 417, 418, 585/654, 656, 658, 661, 943, 700

[56] References Cited

U.S. PATENT DOCUMENTS

| | | | |
|---|---|---|---|
| 4,205,194 | 5/1980 | Mitchell, III et al. | 585/500 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,495,374 | 1/1985 | Jones et al. | 585/500 |
| 4,499,322 | 2/1985 | Jones et al. | 585/500 |
| 4,523,049 | 6/1985 | Jones et al. | 585/500 |
| 4,544,786 | 10/1985 | Breder, Jr. et al. | 585/500 |
| 4,544,787 | 10/1985 | Breder, Jr. | 585/500 |
| 4,547,611 | 10/1985 | Jones et al. | 585/500 |

OTHER PUBLICATIONS

Hinsen et al., Proceedings of the "8th International Congress on Catalysts", vol. III, 1984, pp. III-581-III--592.

Keller et al., "Synthesis of Ethylene via Oxidative Coupling of Methane", Journal of Catalysis 73, 9-19 (1982), pp. 9-19.

Inui et al., "Olefins from Methanol by Modified Zeolites", Petrochemical Developments, Hydrocarbon Procesing, Nov. 1982, pp. 117-120.

Y. C. Hu, "Unconventional Olefin Processes", Hydrocarbon Processing, May 1983, pp. 88-96.

*Primary Examiner*—William R. Dixon, Jr.
*Assistant Examiner*—James M. Hunter, Jr.
*Attorney, Agent, or Firm*—Parkhurst, Oliff & Berridge

[57] ABSTRACT

A process for the preparation of ethane and ethylene by oxidation of methane with oxygen at a temperature of 600° to 900° C., in which lead (II) oxide is used as catalyst (a) dispersed on a carrier of pumice, silicon carbide, zinc oxide, zirconium dioxide, and/or oxides of alkaline-earth elements, or (b) in a mixture with manganese (II) oxide dispersed on a carrier of pumice, silicon carbide, silicon dioxide, titanium dioxide, zirconium dioxide, zinc oxide, and/or oxides of alkaline-earth elements, or (c) without a carrier in a mixture with sodium silicate alone or in combination with silicon dioxide, titanium dioxide, zirconium dioxide, manganese (II) oxide, zinc oxide, and/or oxides of alkaline-earth elements. Ethane and ethylene are obtained with this process in high selectivities with good catalyst activities.

13 Claims, No Drawings

PROCESS FOR THE PREPARATION OF ETHYLENE-ETHANE MIXTURES

TECHNICAL FIELD OF THE INVENTION

The present invention relates to a process for the preparation of ethylene and ethane by oxidative coupling of methane with oxygen or an oxygen-containing gas in the presence of a catalyst.

BACKGROUND OF THE INVENTION

The process for the preparation of ethylene, a starting material with diverse uses in chemical syntheses, are presently almost exclusively based on the cracking of petroleum distillates or natural gas condensates for "wet" gas (ethane and higher hydrocarbons). Elaborate purification steps and gas separation procedures must still follow the industrial cracking process in order to obtain the ethylene in a purity necessary for the further processing. Less elaborate processing steps are necessary for the preparation of ethylene from ethane, but the availability of ethane is limited.

In contrast, methane is a raw material abundantly available in natural deposits. Natural gas contains up to over 90% methane. Therefore, there is interest in developing an economic process for the preparation of ethylene from methane by oxidative coupling.

Many reports have been published on the production of lower olefins from simple starting compounds. Thus, in Hydrocarbon Proc., Nov. 1982, p. 117, T. Inui et al. describe a process in which a mixture of lower olefins is obtained from methanol. In Hydrocarbon Proc., May 1983, p. 88, Y.C. Hu describes a process in which the synthesis gas is converted by the Fischer-Tropsch process into a mixture of olefins, paraffins and carbon dioxide. These processes have the particular disadvantage that the operations must be carried out under pressure and coke formation must be ascertained.

The conversion of methane in the presence of oxygen at atmospheric pressure in one reaction step has already been proposed in the past. Thus, in J. Catal., 73 (1982), pp. 9–19, G. E. Keller and M. M. Bhasin report a process in which the conversion was investigated in the presence of numerous metal oxides as catalyst at 500° to 1000° and a mixture of ethylene and ethane was formed as reaction products in addition to carbon monoxide and carbon dioxide. However, the disadvantage of a very low $C_2$ hydrocarbon selectivity is inherent in this process. To improve selectivity, these authors propose a method with elaborate and costly procedures requiring a high technological outlay.

With reference to the deficiencies of this publication, a process is now proposed in Unexamined West German Patent Application No. 32 37 079, which results in comparable, in part even better, selectivities and higher space-time yields of $C_2$ hydrocarbons even without costly and complex procedures (cf. Unexamined West German Patent Application No. 32 37 079, p. 2, last paragraph, to p. 3, paragraph 3). According to this publication, a process is described for the production of ethane and/or ethylene in which methane and oxygen are reacted in the presence of a catalyst in a fluidized bed or fixed in a reactor at temperatures between 500° and 900° C. within a certain range of partial pressure ratios of methane and oxygen. The catalyst is an oxide of polyvalent metals (cf. Unexamined West German Patent Application No. 32 37 079, p. 3, last paragraph). Cited as preferred catalysts are products with oxides of lead, antimony, tin, bismuth, cadmium, thallium and indium or mixtures thereof as active constituents, lead oxide or a mixture thereof with antimony oxide being especially preferred. The metal oxides can be used as such or dispersed on the surface of a carrier such as aluminum oxide or silicon dioxide (cf. claim 6 and p. 4, paragraph 4). However, as apparent from the results of specific examples in Table 1, even with the particularly preferred lead oxide (on a carrier), a selectivity for hydrocarbons of a maximum of only about 52.9% (7% methane conversion) is achieved. In 1984, at the 8th International Congress on Catalysts in Berlin, W. Hinsen, W. Bytyn, and M. Baerns reported on more extensive research to increase the selectivity. According to the proceedings of the "8th International Congress on Catalysts," Vol. III, pp. 581–592, Verlag Chemie, Weinheim, 1984, the hydrocarbon selectivity of the lead oxide catalyst can be raised by appropriate selection of the carrier and by the addition of alkali. Gamma-aluminum oxide proved the most suitable among the tested carriers: alpha-aluminum oxide, gamma-aluminum oxide, titanium dioxide, aluminum silicate and silica gel; it resulted in maximum selectivity of up to 57.7% (7.1% methane conversion). However, for a commercial exploitation of the process of the oxidative coupling of methane, the need exists for a substantial increase of the selectivity and of the methane conversion.

Therefore, the present invention has as its object the conversion, particularly into $C_2$ hydrocarbons, of methane according to the process of oxidative coupling—whose fundamental principle is known—in a catalyzed reaction with higher selectivities and efficient conversions of methane.

SUMMARY OF THE INVENTION

The above object is achieved with a process for the preparation of ethane and ethylene by oxidation of methane with oxygen or an oxygen-containing gas in the presence of lead (II) oxide as catalyst at a temperature of 600° to 900° C., in which the lead (II) oxide is dispersed on a carrier of pumice, silicon carbide, zinc oxide, zirconium dioxide and/or oxides of alkaline-earth elements, where appropriate in a mixture with sodium silicate, or in a mixture with manganese (II) oxide dispersed on a carrier of pumice, silicon carbide, silicon dioxide, titanium dioxide, zirconium dioxide, zinc oxide and/or oxides of alkaline-earth elements, where appropriate in a mixture with sodium silicate, or without a carrier in a mixture with sodium silicate alone or in combination with silicon dioxide, titanium dioxide, zirconium dioxide, manganese (II) oxide, zinc oxide and/or oxides of alkaline-earth elements.

DETAILED DESCRIPTION OF THE INVENTION

The oxides of magnesium and calcium are preferred as oxides of alkaline-earth elements in all embodiments.

In the embodiment of the invention in which lead (II) oxide is used as catalyst in a mixture with manganese (II) oxide as catalyst, mixtures of lead (II) oxide and manganese (II) oxide at a molar rate of 1:0.1 to 1:3 are preferred. Especially advantageous are mixtures of lead (II) oxide and manganese (II) oxide at a molar ratio of 1:0.2 to 1:0.5, or 1:1.5 to 1:2.

In the embodiments of the invention in which the catalysts are used on a carrier, a proportion of 0.004 to 0.300 mole of catalyst on 100 ml of carrier is preferred. Particularly advantageous is the use of 0.012 to 0.190 mole of catalyst on 100 ml of carrier.

In the embodiment of the invention in which the catalyst is used without a carrier and consists of lead (II) oxide in a mixture with sodium silicate and silicon dioxide, titanium dioxide, zirconium dioxide, zinc oxide and/or oxides of the alkaline-earth elements, mixtures with lead (II) oxide and with these other oxides at a molar ratio of 1:4 to 1:40 are especially suitable.

All of the catalysts according to the invention can be placed in a fluidized bed and in a fixed bed.

The catalysts taught by the invention can be prepared as follows.

If the catalysts are to be employed on a carrier, corresponding soluble compounds of the relevant metals, which release the oxides at fairly elevated temperatures, are dissolved in a suitable solvent, for example, nitrates in water, and the carrier substance is suspended in pellet form in the resulting solution. The solution with a suspended carrier is evaporated to dryness in vacuum and dried in vacuum at about 100° C.

According to the invention, if the catalysts are employed without a carrier, they can be used with a binding agent. In this case, the particular constituents (the oxide of the compounds relating to the particular metal) are made into a paste, for example, in a mortar with sodium silicate, and thoroughly kneaded. Then, a slightly concentrated ammonia solution is added and kneaded in order to initiate the polymerization of the sodium silicate to form the catalyst-binding agent, during which the mass slowly congeals. A metal plate is coated with this mass (in a layer about 5 mm thick). After this layer is dried in vacuum at about 80° C., the resulting brittle catalyst particles are further calcined at about 600° C., then comminuted to the desired particle size.

If necessary, the carriers to be used according to the teachings of the invention may also contain the polymerization product of sodium silicate as a binding agent.

The tests described below were carried out in a quartz tube with an inside diameter of 11.3 mm. After this tube is packed with the catalyst, the latter is brought to the reaction temperature under a nitrogen stream. The tube is heated along a length of 0.5 m in a radiation tube furnace. Methane and oxygen or air are conducted into this reactor through a flow meter and passed over the specific catalyst. The emerging mixture is maintained at a temperature above 80° C. and conducted directly into a gas chromatograph for assaying. This mixture contains as secondary products of the oxidation process carbon monoxide, carbon dioxide, water, ethylene, ethane, and, in fairly small amounts, higher hydrocarbons, especially $C_3$ and $C_4$ hydrocarbons. Soot formation is not demonstrable.

The individual process conditions and results are summarized in Tables 1-5.

The methane-to-oxygen ratio in the charged gas mixture has an appreciable effect on selectivity and conversion, as is evident from Table 1.

TABLE 1

| | 60 g of a catalyst prepared from 13.4 g of PbO, 21.2 g of sodium silicate, 42 g of ZnO, 0.4 ml of concentrated ammonia adjusted to pH = 4 with $HNO_3$ 750° C. no carrier | | | | | | | | |
|---|---|---|---|---|---|---|---|---|---|
| Charging | (liter/h) | Conversion(%) | | Selectivity (%) | | | | | |
| Methane | Air (25° C.) | $CH_4$ | $O_2$ | $CO_2 + CO$ | $C_2H_4$ | $C_2H_6$ | $C_3$ | $C_4$ | ΣHC |
| 66 | 34 | 7.43 | | 25.7 | 35.6 | 35.2 | 3.4 | 0 | 74.2 |
| 50 | 50 | 13.31 | 62.3 | 37.6 | 32.1 | 24.1 | 3.1 | 2.9 | 62.2 |
| 34 | 66 | 20.08 | 59.2 | 48.5 | 30.9 | 18.1 | 2.5 | 0 | 51.5 |
| | Oxygen | | | | | | | | |
| 90 | 10 | 8.09 | 71 | 27.9 | 34.3 | 33.8 | 3.9 | 0 | 72.0 |
| 80 | 20 | 17.70 | 73 | 39.9 | 29.0 | 20.7 | 3.2 | 7.1 | 60.0 |
| 66.6 | 33.3 | 26.34 | 61 | 51.0 | 25.3 | 15.5 | 2.6 | 5.4 | 48.8 |

Thus, selectivity can be improved by reducing the proportion of oxygen, while increasing the proportion of oxygen increases the methane conversion.

Another possibility for further improving the selectivity with a simultaneous increase of the methane conversion is a method using side charging of the oxygen. In this case, only the methane is introduced at one end of the reaction tube, while the total amount of oxygen is charged into the tube uniformly distributed through numerous entry holes in the sides.

The process embodying the invention can be carried out at temperatures of from 600° to 900° C. A temperature range between 650° and 850° C is preferred.

The effect of temperature on the oxidative coupling of methane with a catalyst according to the invention is illustrated in Table 2.

TABLE 2

| | 45 g of the catalyst used in Table 1 33 liters/h of $CH_4$, 66 liters/h of air (at room temperature) | | | | | | | |
|---|---|---|---|---|---|---|---|---|
| | $O_2$ conversion | $CH_4$ conversion | Selectivity (%) | | | | | |
| T(°C.) | (%) | (%) | $CO + CO_2$ | $C_2H_4$ | $C_2H_6$ | $C_3$ | $C_4$ | ΣHC |
| 650 | 4 | 1.1 | 37.3 | 20.9 | 41.8 | 0 | 0 | 62.7 |
| 700 | 18 | 3.3 | 25.3 | 24.4 | 50.5 | 0 | 0 | 74.9 |
| 750 | 95 | 12.3 | 25.4 | 36.3 | 32.0 | 4.0 | 2.3 | 74.6 |
| 800 | 95 | 13.6 | 27.2 | 41.3 | 28.0 | 3.9 | 1.7 | 74.9 |
| 850 | 95 | 12.5 | 27.8 | 43.9 | 21.0 | 5.0 | 2.3 | 72.2 |

Therefore, it appears that higher proportions of ethylene are produced at fairly high temperatures and the proportion of ethane declines accordingly; the sum of ethylene and ethane remains almost constant.

The pH during the preparation of the catalyst also has an effect on the selectivity. The results of tests with the catalysts incorporating the invention are apparent from Table 3, to which, during preparation, certain amounts of calcium oxide or nitric acid were added to obtain a particular pH.

TABLE 3

45 g of catalyst used in Table 1
pH = 12 initially; adjustment of specific pH by addition of CaO or HNO₃
33 liters/h of CH₄, 66 liters/h of air
(at room temperature)
750° C.

| pH | Conversion (%) $CH_4$ | $O_2$ | $C_2$—HC—Selectivity (%) |
|---|---|---|---|
| 12.5 | 10.8 | 95 | 58 |
| 9 | 11.1 | 95 | 64 |
| 6.5 | 12.3 | 95 | 67 |
| 4 | 13.4 | 95 | 70 |
| 3 | 9.1 | 81 | 64 |

The results of tests with other numerous catalysts or combinations of catalysts and carriers are summarized in Tables 4 and 5 below.

TABLE 4 about 50 ml of catalyst (active components and carrier)
0.06 moles of active components on 60 ml of carrier
66 liters of methane/h
33 liters of air (25° C.)/h
750° C.

| Test No. | Catalysts* (active components) | Carrier | Conversion $CH_4$ (%) | $C_2$—HC—Selectivity (%) |
|---|---|---|---|---|
| 1 | PbO | Zinc oxide | 11.8 | 69 |
| 2 | PbO | Magnesium oxide | 10.8 | 59 |
| 3 | PbO | Calcium oxide | 10.6 | 60 |
| 4 | PbO | Zirconium oxide | 11.8 | 60 |
| 5 | PbO | Zinc oxide bound to sodium silicate | 10.2 | 73 |
| 6 | PbO | Silicon carbide | 9.6 | 69 |
| 7 | PbO | Pumice | 0.6 | 95 |
| 8 | PbO:MnO (1:2) | Silica gel** | 9.1 | 58 |
| 9 | PbO:MnO (5:1) | Silica gel** | 12.6 | 70.5 (with $C_3$—HC:73.7) |

*Numbers given in parentheses = molar ratios
**Silica gel EM from Gebr. Herrmann Co., Cologne-Ehrenfeld

TABLE 5 about 45 ml of catalyst prepared with sodium silicate
no carrier 66 liters of methane/h
750° C. 33 liters of air(25° C.)/h

| Test No. | Catalyst* | pH of catalyst preparation | Conversion $CH_4$ | $C_2H_4$ | $C_2H_6$ | $C_3H_8$ | $C_4H_{10}$ | ΣHC |
|---|---|---|---|---|---|---|---|---|
| 1 | PbO | 12 | 0.3 | 66 | 0 | 0 | 0 | 66 |
| 2 | PbO:ZnO (1:8) | 4 | 12.3 | 36.3 | 32.0 | 4.0 | 2.3 | 74.6 |
| 3 | PbO:ZnO (1:40) | 4 | 11.4 | 25.5 | 37.7 | 8.2 | 0 | 71.4 |
| 4 | PbO:ZnO:ZrO₂ (1:4:3) | 12 | 4.3 | 17.0 | 60.5 | 0 | 0 | 77.5 |
| 5 | PbO:TiO₂ (1:8) | 4 | 6.3 | 24.9 | 46.9 | 3.6 | 0 | 75.4 |
| 6 | PbO:ZrO₂ (1:4) | 4 | 10.2 | 31.8 | 33.4 | 3.7 | 0 | 68.9 |
| 7 | PbO:MgO (1:8) | 12 | 9.4 | 12.0 | 40.0 | 1.4 | 0 | 53.4 |
| 8 | PbO:CaO (1:8) | 7 | 10.9 | 19.0 | 45.3 | 0 | 0 | 64.3 |
| 9 | PbO:MnO (1:2) | 12 | 10.6 | 21.9 | 40.4 | 3.0 | 0 | 65.3 |
| 10 | PbO:MnO:ZnO (3:1:25) | 4 | 12.2 | 23.3 | 42.8 | 2.9 | 0 | 69.0 |

*Numbers given in parentheses = molar ratios

The reaction conditions especially available for specific targets in relation to the composition of the end product are readily apparent from Tables 1, 2 and 5. The following composition of the end product (HC selectivities) was determined for Test 9 in Table 4: 32.5% $C_2H_4$, 38.0% $C_2H_6$ and 3.2% $C_3$ Thus, by appropriate selection of the methane to oxygen (or air) ratio, the temperature and the catalyst, a preferred ethylene-to-ethane ratio can be obtained or, if so desired, the proportion of hydrocarbons with more than two carbon atoms can be reduced.

According to the invention, in many cases very high hydrocarbon selectivities >70% are obtained with good catalyst activities. In other cases, even a selectivity >90% is obtained with a low activity of the catalyst. Depending on the carrier employed, it can be said of the lead-oxide catalyst on a carrier that a high selectivity can be obtained with a good activity (e.g., zinc oxide as carrier) or a very high selectivity with a low activity (e.g., pumice as carrier).

Therefore, the process taught by the invention is superior to processes of the prior art and is suitable for economic preparation of ethane and ethylene by oxidative coupling of methane.

To this end, procedures with a low proportion of oxygen in the reactor are recommended such as, for example, can be achieved with a fluidized bed reactor, a recycle reactor, side charging, or other means to handle the concentration. In industrial procedures, the reaction mixture can be separated by conventional refinery gas technology or can be converted without separation into, for example, chlorinated products.

We claim:

1. A process for the preparation of ethane and ethylene, comprising oxidizing methane with oxygen or an oxygen-containing gas at a temperature of 600° to 900° C. in the presence of a catalyst consisting essentially of lead (II) oxide in a form selected from the group consisting of:

(a) dispersed on a carrier comprising at least one member selected from the group consisting of pumice, silicon carbide, zinc oxide, zirconium dioxide and oxides of alkaline-earth elements;

(b) in a mixture with manganese (II) oxide dispersed on a carrier comprising at least one member selected from the group consisting of pumice, silicon carbide, silicon dioxide, titanium dioxide, zirconium dioxide, zinc oxide and oxides of alkaline-earth elements; and (c) in a mixture with sodium silicate alone or in combination with at least one member selected from the group consisting of silicon dioxide, titanium dioxide, zirconium dioxide, manganese (II) oxide, zinc oxide and oxides of alkaline-earth elements.

2. The process as set forth in claim 1, wherein said methane is oxidized at 650° to 850° C.

3. The process as set forth in claim 1, wherein said oxides of alkaline-earth elements are selected from the group consisting of oxides of magnesium and oxides of calcium.

4. The process as set forth in claim 1, wherein said catalyst comprises a mixture of lead (II) oxide and manganese (II) oxide at a molar ratio of 1:0.1 to 1:3.

5. The process as set forth in claim 1, wherein said catalyst comprises a mixture of lead (II) oxide and manganese (II) oxide at a molar ratio selected from the group consisting of 1:0.2 to 1:0.5 and 1:1.5 to 1:2.

6. The process as set forth in claim 1, wherein said catalyst comprises 0.004 to 0.300 mole of said lead (II) oxide per 100 ml of said carrier.

7. The process as set forth in claim 1, wherein said catalyst comprises 0.004 to 0.300 mole of said mixture of lead (II) oxide with manganese (II) oxide per 100 ml of said carrier.

8. The process as set forth in claim 1, wherein said catalyst comprises 0.012 to 0.190 mole of said lead (II) oxide per 100 ml of said carrier.

9. The process as set forth in claim 1, wherein said catalyst comprises 0.012 to 0.190 mole of said mixture of lead (II) oxide with manganese (II) oxide per 100 ml of said carrier.

10. The process as set forth in claim 1, wherein said lead (II) oxide dispersed on a carrier is in a mixture with sodium silicate.

11. The process as set forth in claim 1, wherein said mixture of lead (II) oxide with manganese (II) oxide dispersed on a carrier is in a mixture with sodium silicate.

12. A process for the preparation of ethane and ethylene, comprising oxidizing methane with oxygen or an oxygen-containing gas at a temperature of 600° to 900° C. in the presence of a catalyst comprising lead (II) oxide in a mixture with sodium silicate alone or in combination with at least one member selected from the group consisting of silicon dioxide, titanium dioxide, zirconium dioxide, manganese (II) oxide, zinc oxide and oxides of alkaline-earth elements.

13. The process as set forth in claim 12, wherein said catalyst comprises a mixture of lead (II) oxide with sodium silicate and at least one member selected from the group consisting of silicon dioxide, titanium dioxide, zirconium dioxide, zinc oxide and oxides of alkaline-earth elements at a molar ratio of lead (II) oxide to the other compounds of 1:4 to 1:40 in the absence of a carrier.

* * * * *

UNITED STATES PATENT AND TRADEMARK OFFICE
CERTIFICATE OF CORRECTION

PATENT NO. : 4,783,572
DATED : November 8, 1988
INVENTOR(S) : Klaus WOHLFAHRT et al It is certified that error appears in the above-identified patent and that said Letters Patent is hereby corrected as shown below:

Column 5, line 65, change "$C_3$" to --$C_3H_8$.--.

Signed and Sealed this

Twenty-ninth Day of August, 1989

*Attest:*

DONALD J. QUIGG

*Attesting Officer*  *Commissioner of Patents and Trademarks*